United States Patent [19]

Gibbs et al.

[11] Patent Number: 4,994,065
[45] Date of Patent: Feb. 19, 1991

[54] APPARATUS FOR DISPENSING LOW VISCOSITY SEMI-FLUID MATERIAL UNDER PRESSURE

[75] Inventors: Rebecca Gibbs, Carrboro, N.C.; Jan J. Krygier, St. Constant, Canada; Joseph E. Miller, deceased, late of Carrboro, N.C.; L. A. Desrochers, executor; Bryan O'Donnell, executor, both of Edmonton, Canada; Patricia Miller, executor, Westmount, Canada

[73] Assignee: Zimmer, Inc., Warsaw, Ind. ; by said Rebecca Gibbs

[21] Appl. No.: 524,793

[22] Filed: May 18, 1990

[51] Int. Cl.$^5$ .............................................. A61F 5/04
[52] U.S. Cl. ........................................ 606/92; 606/93; 606/94; 222/391; 604/209; 604/61
[58] Field of Search ................... 604/209, 61; 606/94, 606/92, 93, 95; 633/16; 222/391

[56] References Cited

U.S. PATENT DOCUMENTS

| | | | |
|---|---|---|---|
| 4,338,925 | 7/1982 | Miller | 606/61 X |
| 4,406,654 | 9/1983 | Bristow | 604/209 |
| 4,425,121 | 1/1984 | Young et al. | |
| 4,472,141 | 9/1984 | Dragan | |
| 4,546,767 | 10/1985 | Smith | 606/93 |
| 4,569,662 | 2/1986 | Dragan | |
| 4,671,263 | 6/1987 | Draenert | 606/94 |
| 4,744,494 | 5/1988 | Seager et al. | 222/391 |

FOREIGN PATENT DOCUMENTS 2814353 10/1978 Fed. Rep. of Germany ........ 606/93
2107989A 5/1983 United Kingdom .

Primary Examiner—Robert A. Hafer
Assistant Examiner—Kerry Owens
Attorney, Agent, or Firm—Foley & Lardner, Schwartz, Jeffery, Schwaab, Mack, Blumenthal & Evans

[57] ABSTRACT

An injection gun especially useful for injecting low volume, high pressure shots of bone cement. The gun includes a cylindrical housing with a plunger including a plunger rod extending axially through the housing. The plunger rod includes a segment which is provided with an axial series of notches. A ratchet block is slidable axially within the cylindrical housing and is concentric with the plunger rod. The ratchet cylinder mounts at least a ratchet pawl urged against the plunger rod and adapted to engage and lock into the series of notches for forward movement. A pistol grip extends from the cylindrical housing, and a lever is pivoted thereto with an extension of the lever engaging the ratchet cylinder for advancing the plunger. A second ratchet pawl is mounted on a fixed member of the cylindrical housing for retaining the plunger against rearward movement when the pawl in the ratchet cylinder is disengaged from the rod.

10 Claims, 2 Drawing Sheets

4,994,065

APPARATUS FOR DISPENSING LOW VISCOSITY SEMI-FLUID MATERIAL UNDER PRESSURE

BACKGROUND OF THE INVENTION

1. Field of the Invention

The present invention relates to a feeding device for delivering low viscosity paste material under pressure, and more particularly, to an improved manual dispensing mechanism therefor.

2. Description of the Prior Art

There exist various types of hand-operated paste material dispensing devices of the caulking gun variety which include a plunger adapted to advance axially through a cylinder to which the end of a paste material cartridge is attached. The plunger is advanced by a trigger-type lever pivoted to a pistol grip, and a ratchet device is mounted to the end of the lever for engaging a rod forming part of the plunger.

Such a dispensing device is advantageously used in the delivery of bone cement into cavities formed in a bone to which a prosthesis is to be mounted. An example of such an apparatus and method is described in U.S. Pat. No. 4,338,925, issued July 13, 1982 to Jo Miller, one of the co-inventors of the present invention. This patent is incorporated herein by reference. The Miller patent describes a high pressure injection gun including a housing axially supporting a plunger and rod. A hardened steel disc with a central opening rests on the rod. Contraction of the lever against the pistol grip causes the disc to tilt, lock onto the rod, and move the rod forward while compressing an axially aligned return spring. When the trigger is released, the return spring presses against the disc, releasing it from engagement on the rod and forcing it to slide on the rod to its initial position while returning the lever.

It has been found that there is a considerable amount of lost-motion in tilting the disc. For instance, one third of the travel of the lever can be lost-motion. Furthermore, when the edges of the disc defining the central opening have been worn, the disc can slip on the rod, which can be a serious situation in the middle of a surgical operation.

Other injection guns exist, such as the type described in U.S. Pat. No. 4,406,654, issued Sept. 27, 1983 to Robert L. Bristow. In this patent, spring mounted pawls are used which engage notches in the rod. One of the pawls is pivotally mounted to the lever. Since the rod is of relatively small diameter, the lever beyond the pivot point must be longer for the same amount of travel, and thus the pressure applied tends to be less. Although the ratchet and notch principle used in Bristow and in a caulking gun is an improvement, the mechanical advantage provided by the disc in the Miller U.S. Pat. No. 4,338,925 is lost. In the Miller patent, the disc, when engaged on the rod, effectively increases the diameter of the rod. Only a short extent of the lever is necessary above the pivot point to provide a low volume, high pressure shot of cement.

SUMMARY OF THE INVENTION

It is an aim of the present invention to provide an improved cement injection gun of the type described above.

More particularly, it is an aim of the present invention to take advantage of the positive engagement provided by Bristow, yet have the mechanical advantage of Miller.

It is a further aim of the present invention to provide an improved injection gun mechanism for various applications, where a low volume, high pressure shot of paste material is required.

A construction in accordance with the present invention comprises a housing for engaging the end of a cartridge from which a low viscous paste material is to be dispensed. A plunger including a rod slides axially of the housing for engagement within the cartridge. The rod is provided with a series of notches forming teeth, and the notches are discontinuous at least in a circumferential sector extending axially, leaving a smooth rod surface. An annular ratchet cylinder is slidable on the rod within the housing. The housing has a pistol grip extending at an angle to the axis thereof, and a lever is pivotally mounted to the pistol grip with the lever extending beyond the pivot point thereof to engage the ratchet cylinder. The ratchet cylinder pivotally mounts at least a pawl which is spring biased to engage the notches on the rod in order to advance the plunger.

In a more specific embodiment, the housing is provided with a fixed member forward of the ratchet cylinder, and a second spring biased pawl is mounted to the fixed member and urged towards the rod to engage the teeth thereon.

The advantage of the present invention as described herein is that a highly efficient axial drive with little lost-motion is provided as a result of the large diameter ratchet cylinder including the flange relative to the diameter of the plunger rod. Since ratchet pawls are utilized within the ratchet cylinder to engage teeth on the plunger rod, the possibility of slippage has been overcome.

BRIEF DESCRIPTION OF THE DRAWINGS

Having thus generally described the nature of the invention, reference will now be made to the accompanying drawings, showing by way of illustration, a preferred embodiment thereof, and in which.

DESCRIPTION OF THE PREFERRED EMBODIMENTS

Figure 1:
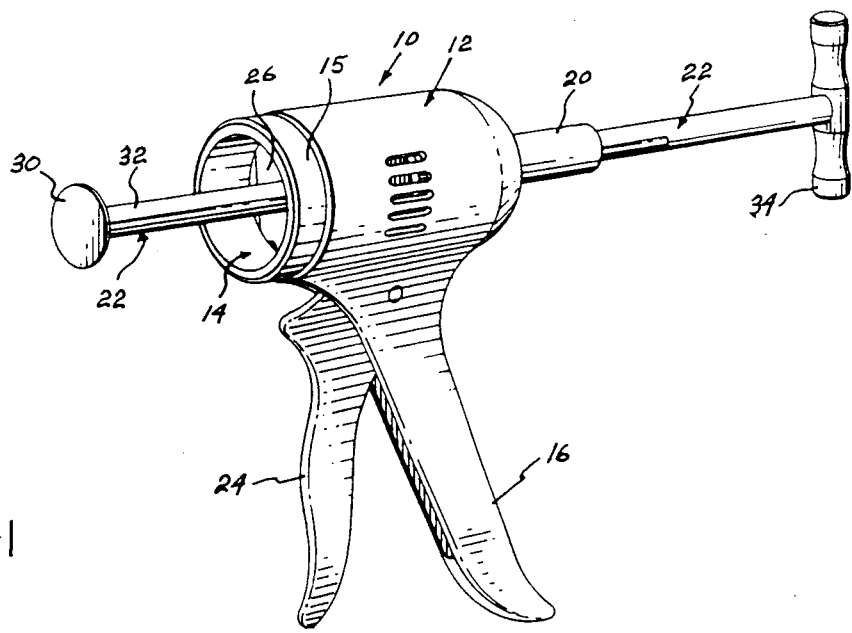
FIG. 1 is a perspective view of an embodiment in accordance with the present invention.

According to the embodiment shown in the drawings, there is shown an injector gun 10 of the type used for applying bone cement under high pressure into the cavity of a bone in an environment as described in U.S. Pat. No. 4,338,925. The injector gun 10 includes a housing 12 defining a cavity 14 within the cylinder 18. A removable bezel 15 is provided in the cavity 14 in order to mount a cement cartridge (not shown). The housing 12 also includes a pistol grip 16 to which is pivoted a trigger lever 24. A plunger 22 slides axially of the cylinder 18 and through a tube 20 which extends rearwardly of the cylinder 18.

The cavity 14 within the cylinder 18 is divided by a partition plate 26 which has an opening 27 to allow the passage of the plunger 22. Bolts 28a mount the partition plate 26 to guide members 28 fixed to the housing 18. The function of guide members 28 will be evident further.

The bezel 15 has a bayonet connection for engaging the projections 15a on the wall of cylinder 18.

The plunger 22 includes an elongated rod 32 of circular cross-section, and a plunger plate 30 mounted at the front end thereof. A handle 34 is provided at the other end of the rod 32. An elongated axially extending segment of the rod 32 includes a series of notches 36 which define teeth 38. At the rear end of the series of notches 36, there is provided a release recess 37.

An elongated axial groove 39 is also defined in the rod 32 in another segment of the rod.

The partition wall 26 mounts a cylindrical collar 40 within which there is provided a pawl 42 mounted on a pivot pin 46 within the collar. The pawl 42 is maintained under clockwise torsional pressure by a spring 44 against the rod 32.

Figure 2:
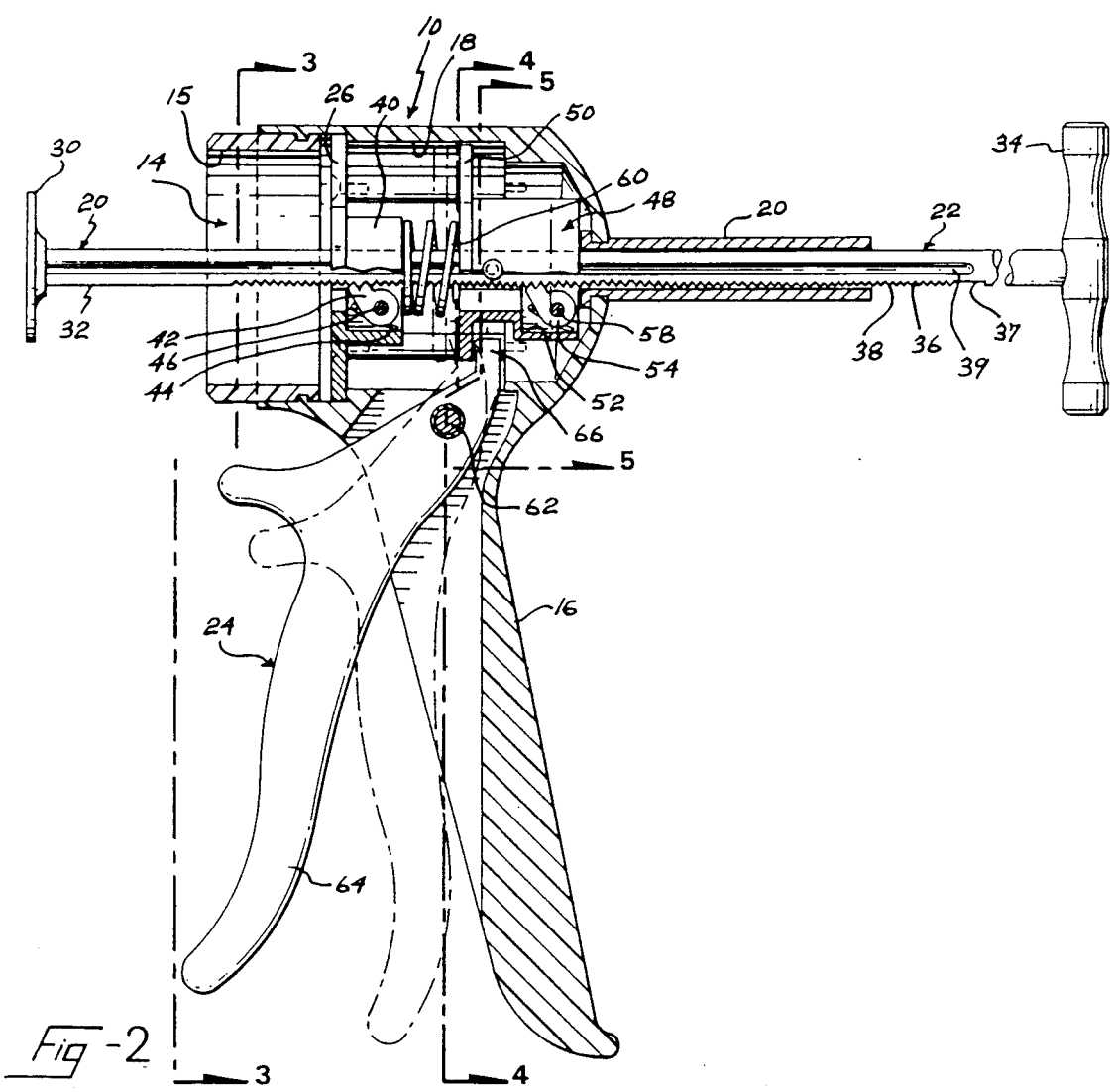
FIG. 2 is an axial cross-section taken through the device shown in FIG. 1.
Figures 3, 4:
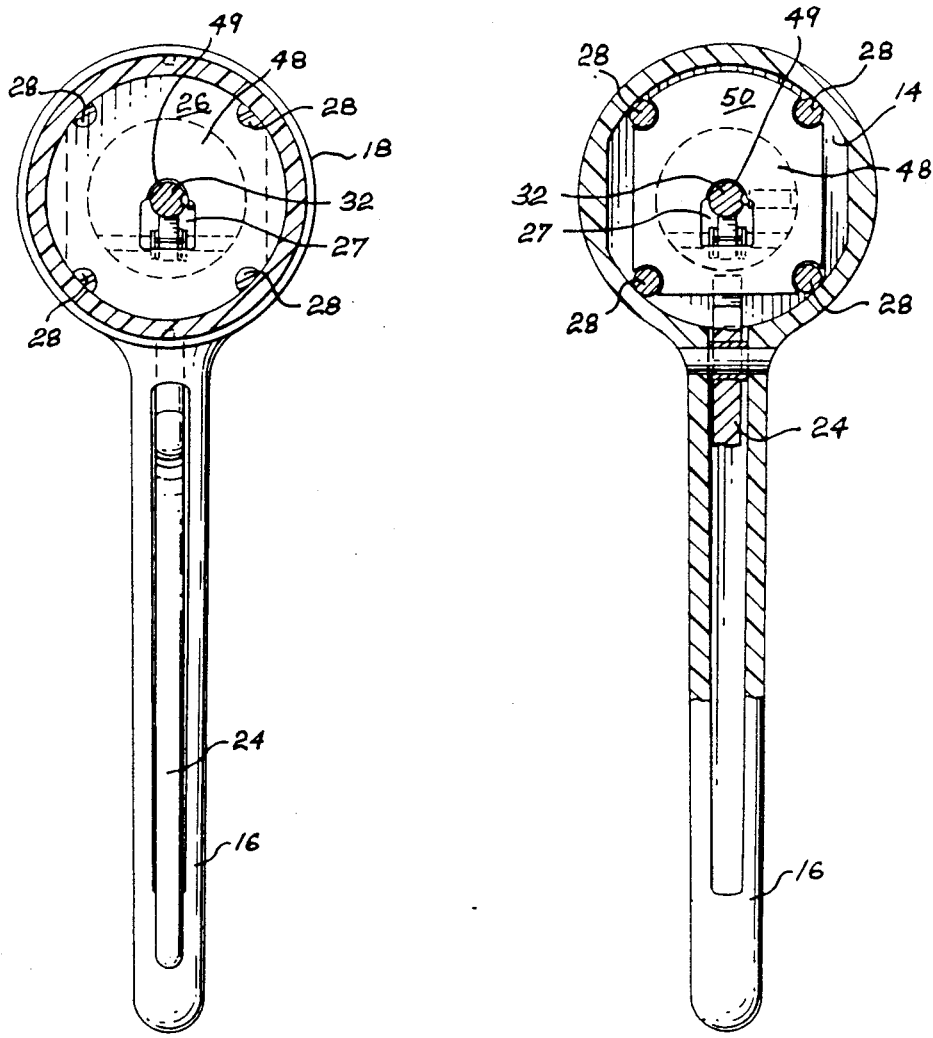
FIG. 3 is a vertical cross-section taken through line 3—3 of FIG. 2.
FIG. 4 is a vertical cross-section taken along line 4—4 of FIG. 2.

A ratchet cylinder 48 is adapted to slide within the cavity 14 of the housing 18 on the guide members 28, as shown in FIG. 4. The rod 32 passes through a bore 49 in the ratchet cylinder 48. The ratchet cylinder 48 also includes a radially extending flange 50. The cylinder 48 defines a cavity 52 wherein a pawl 54 is pivotally mounted on a pivot pin 58 and urged in a clockwise direction by a spring 56 to engage the teeth 38 on rod 32. The cylinder 48 is urged rearwardly from the partition wall 26 by means of a compression spring 60, as shown in FIG. 2.

The trigger lever 24 is pivotally mounted on pivot pin 62 to the pistol grip 16 and includes a lever grip 64 on one side of the pivot pin 62 and an engagement finger 66 on the other side of the pivot pin 62. The finger 62 engages the flange 50 on the ratchet cylinder 48.

Figure 5:
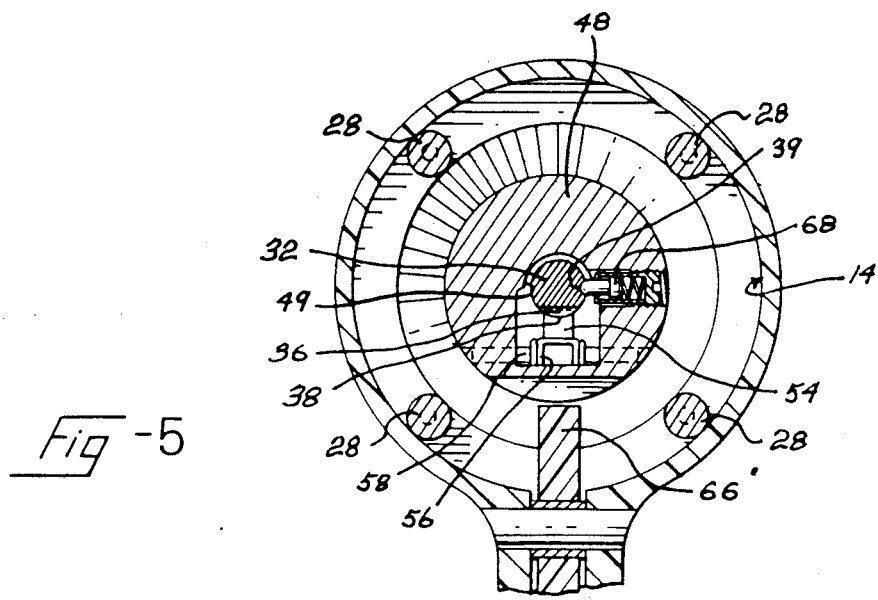
FIG. 5 is a vertical cross-section taken along line 5—5 of FIG. 2.

A spring plunger, as shown in FIG. 5, is adapted to snap into the groove 39.

Thus, in operation, a cartridge having a radial flange (not shown) can be inserted within the cavity 14 and retained therein by the bezel 15. When it is required to advance the plunger 22 through the cartridge, the trigger lever 24 is contracted counter-clockwise against the pistol grip 16, causing the finger 66 to advance against the flange 50 of the ratchet cylinder 48. The pawl 54 engages the teeth 38 on the rod 32, and as the cylinder 48 is being advanced axially within the cavity 14 by means of the finger 66 acting on the flange 50, the rod 32 is also being advanced. In this forward direction, the cylinder 48 compresses the spring 60 against the partition wall 26.

When the trigger lever grip 64 has reached its fully retracted position against the pistol grip 16, it is then released. The spring 60 will immediately return the ratchet cylinder 48 rearwardly entraining the finger 6, thereby forcing the lever grip 64 to return to its original position. The pawl 54 will automatically disengage itself from the teeth 38 as the cartridge 48 is returned, but under the constant urging of the spring 56, it will engage the teeth 38 as soon as the travel of the ratchet cylinder 48 has terminated. The rod 32 will remain immobile since the pawl 42 will have engaged the teeth 38, locking the rod 32 against rearward movement. It is only under the action of the lever 24 and the pawl 54 that the rod 32 will advance, causing the pawl 42 to disengage itself from the teeth 38 but always being urged against the teeth 38 by means of the spring 44 to thereby engage the teeth 38 as soon as the forward travel of the rod 32 has stopped.

This action is repeated until either the plunger 22 has reached its forwardmost extent or enough bone cement has been inserted into a particular bone cavity. In order to retract the plunger 22, it is necessary to rotate the handle 34, thus rotating the rod 32 until the teeth 38 are clear of the pawls 42 and 54. The rod 32 can be pulled back manually through the housing 18.

When it is required to initiate a further advance of the plunger 22, the handle 34 is again rotated until the spring plunger 68 engages the groove 39 provided in the rod. Once the spring plunger 68 has been centered in the groove 39, the segment of the rod containing the series of notches and teeth 36 and 38 will coincide with the pawls 42 and 54. The action of advancing the plunger 22 can again be commenced.

It is clear that the injection gun can be used in other applications besides the insertion of bone cement in the bone. A similar injector gun can easily be adapted to all kinds of uses, such as a caulking gun or other types of guns where a controlled dosage of a paste material is required.

By paste material, one means any type of low viscous cement or semi-fluid material, such as gels, pastes, etc.

In an example of the present embodiment wherein the injection gun is used for bone cement, it has been found that a satisfactory pressure was obtained with almost no lost-motion by having a gun wherein the ratio of the lever grip 64 to the finger 66 is approximately 10:1 while the diameter of the ratchet cylinder is 1.1 inches with the flange extending to a total vertical dimension of 1.7 inches. The diameter of the rod 32 is 0.30 inches.

Accordingly, the ratchet cylinder 48 including the flange 50 increases the relative diameter of the rod three to four times, thereby allowing a relatively large mechanical leverage advantage.

Although the ratchet cylinder 48 has been illustrated with a single pawl 52, it is understood that several variations can be contemplated, such as providing at least one pawl on diametrically opposed segments of the ratchet cylinder engaging respective teeth on the rod 32. Likewise, at least a pair of pawls 52 can be provided in axial alignment within the ratchet cylinder 48, and one of the pawls could be out of phase with the other pawl.

It is also contemplated that the lever 24 may be constructed so that the lever ratio might change; for instance, the finger 66 can be made telescopic so as to vary the travel of the ratchet cylinder and the pressure applied thereto.

We claim:

1. A feeding device for delivering a low viscosity paste material under pressure comprising a housing adapted to engage the end of a cartridge from which the low viscosity paste material can be dispensed, a plunger including a rod adapted to slide axially of the housing for engagement within the cartridge, the rod being provided with an axially extending series of notches forming teeth and the notches being discontinuous at least in a circumferential segment of the rod leaving a smooth axial rod surface segment) an annular ratchet cylinder slidable within the housing, the ratchet cylinder including a bore through which the rod is to pass, a pistol grip extending from the housing at an angle to the axis of the housing, and a lever pivotally mounted to the pistol grip with the lever extending beyond the pivot point thereof to engage the ratchet cylinder, the ratchet cylinder including a pawl pivotally mounted therein and being spring biased to engage the series of teeth on the rod in order to advance the plunger.

2. A feeding device as defined in claim 1, wherein a fixed member is provided in the cavity of the housing and a second ratchet pawl is pivotally mounted to the fixed member and urged by a spring in a clockwise direction against the rod to engage the teeth on the rod to prevent rearward movement of the rod when the first pawl is disengaged from the teeth.

3. A feeding device as defined in claim 2, wherein the fixed member is a radially extending partition wall provided in the cavity forward of the ratchet cylinder, and a cylindrical collar is mounted to said partition wall and surrounding the plunger rod and said second ratchet pawl is pivotally mounted in the cylindrical collar.

4. A feeding device as defined in claim 3, wherein a compression spring extends between the cylindrical collar and the ratchet cylinder to urge the ratchet cylinder rearwardly against the action of the trigger lever.

5. A feeding device as defined in claim 1, wherein the ratchet cylinder is slidable axially within the housing guided by a plurality of spaced-apart guide members parallel to the axis of the housing and mounted within the cavity.

6. A feeding device as defined in claim 1, wherein the plunger rod defines an elongated axial groove in a segment thereof separate from the series of notches and a spring plunger is mounted in the ratchet cylinder adapted to engage the elongated groove such that when the spring plunger is engaged in the elongated groove, the series of notches coincide with the pawl.

7. A feeding device in accordance with claim 1, wherein the device is in the form of an injection gun for injecting bone cement from a cartridge.

8. An injection gun as defined in claim 7, wherein the lever ratio of the trigger lever is 1:10.

9. An injection gun as defined in claim 8, wherein the ratio of the diameter of the ratchet cylinder to the diameter of the rod is between 3:1 and 4:1.

10. An injection gun as defined in claim 9, wherein the ratchet cylinder includes a radial flange and the lever extension engages the flange of the ratchet cylinder.

* * * * *